United States Patent [19]

Larson et al.

[11] Patent Number: 5,185,142

[45] Date of Patent: Feb. 9, 1993

[54] ANTIGEN-SPECIFIC COMPOSITION AND IN VIVO METHODS FOR DETECTING AND LOCALIZING AN ANTIGENIC SITE AND FOR RADIOTHERAPY

[75] Inventors: Steven M. Larson, Washington, D.C.; Ronald Finn, Bethesda, Md.; Jorge A. Carrasquillo; James C. Reynolds, both of Rockville, Md.; Ronald D. Neumann, Potomac, Md.; Martin C. Graham, Larchmont; Keith S. Pentlow, Forest Hills, both of N.Y.

[73] Assignee: The United States of America as represented by the Secretary of the Department of Health and Human Services, Washington, D.C.

[21] Appl. No.: 386,095

[22] Filed: Jul. 28, 1989

[51] Int. Cl.$^5$ .................. A61K 49/02; C07K 15/00
[52] U.S. Cl. .................. 424/1.1; 530/388.8; 530/391.3; 600/3; 600/4
[58] Field of Search .................. 424/1.1, 85.91, 9; 530/389, 388.8, 391.3; 600/3, 4

[56] References Cited

U.S. PATENT DOCUMENTS

| | | | |
|---|---|---|---|
| 4,444,744 | 4/1984 | Goldenberg | 424/1.1 |
| 4,454,106 | 6/1984 | Gasnow et al. | 424/1.1 |
| 4,460,561 | 6/1984 | Goldenberg | 424/1.1 |
| 4,820,505 | 4/1989 | Ginsberg et al. | 424/1.1 X |
| 4,876,081 | 10/1989 | Wilbur et al. | 424/1.1 |
| 4,917,878 | 4/1990 | Thakur | 424/1.1 |
| 4,937,183 | 6/1990 | Ultee | 530/389 |

OTHER PUBLICATIONS

CA 109(19):166406f, McGarry et al., (1988) *Med. Sci. Res*, vol. 16, No. 14 pp. 737–738.
CA 113(3):20220b, Goethals et al., (1990) *Eur. J. Nucl. Med.*, 16(4–6), pp. 237–240.
CA 111(13):111619p, Welch et al., (1988) *NATO ASI Ser.*, Ser. A, 152, pp. 261–267.
CA 102(11):92222z, Weinreich, (1984) *Radioakt. Isot. Klin. Forsch.*, 16(2) 555–63.
Eary et al., *J. Nucl. Med.*, vol. 27(6), abstract No. 437, "Production of Positron Emitting Zr-89 . . . ", p. 983 (1986).
Miraldi et al., *J. Nucl. Med.*, vol. 28(6), Posterboard 882, "Position Imaging of Neuroblastoma Tumors . . . ", p. 1078 (1987).
Jacobson, *JAMA*, vol. 259(14), "Positron Emission Tomography in Oncology", pp. 2126–2131 (1988).
McGarry et al., *Med. Sci. Res.*, vol. 16, "$^{124}$-I-Iodinated N-succinimidyl-3-hydroxyphenyl propionate labelling . . . ", pp. 737–738 (1988).
Goodwin, *J. Nucl. Med.*, vol. 28(8), "Editorial: Pharmacokinetics and Antibodies," pp. 1358–1362 (1987).
E. E. Williams "Tumor Imaging with Radioactive Metal Chelates Conjugated to Monoclonal Antibodies", Science, vol. 215, Mar. 19, 1982.

*Primary Examiner*—Robert L. Stoll
*Assistant Examiner*—John M. Covert
*Attorney, Agent, or Firm*—Lowe, Price, LeBlanc & Becker

[57] ABSTRACT

A composition comprises an antigen-specific antibody or antigen-binding fragment thereof labeled with Iodine-124 at a site other than, and which does not significantly interfere with, the antibody-antigen binding site. An in vivo method of radiotherapy directed to an antigenic site comprises administering to a subject in need of the therapy an amount of the antigen-specific composition described above effective to attain a reduction of the size of a tumor associated with the antigen. An in vivo method for detecting and localizing an antigenic site in a subject in need of such detection comprises administering to the subject an amount of the antigen-specific composition of the invention effective to localize the antigen-antibody binding site and scanning the subject's body with a positron-emitter detector to attain the localization of the site. An in situ method of radiotherapy directed to an antigenic site in a subject in need of such therapy comprises detecting and localizing the site by the in vivo method described above and thereafter in situ delivering a positron-emitting labeled antibody chelate capable of binding to either the I-124 labeled antibody or fragment thereof, or to the antigen at a site other than the antibody-antigen binding site.

7 Claims, 4 Drawing Sheets

```
RAW DATA FROM VL8FILE.DAT; 37         FRAME   1, PLANE  7
DATA COLLECTED ON 28-DEC-88 FROM 19:39:21 TO  19:44:14
      UNSCRAMBLED, WOBBLE CORRECTED          AVG CT:      16
                                             STD DEV:     44
                                      -00    PEAK CT:    305
                                      -05    TOTAL CTS:  125782
```

```
                                      -10
                                      -15
                                      -20
                                      -25
                                      -30
                                      -35
                                      -40
                                      -45
```

```
RAW DATA FROM VL8FILE.DAT; 40         FRAME   1, PLANE  7
DATA COLLECTED ON 28-DEC-88 FROM 19:48:22 TO  19:53:15
      UNSCRAMBLED, WOBBLE CORRECTED          AVG CT:      16
                                             STD DEV:     44
                                      -00    PEAK CT:    283
                                      -05    TOTAL CTS:  125243
```

```
                                      -10
                                      -15
                                      -20
                                      -25
                                      -30
                                      -35
                                      -45
                                      -45
```

```
RAW DATA FROM VL8FILE.DAT;41      FRAME 1, PLANE 7
DATA COLLECTED ON 28-DEC-88 FROM 20:6:41 TO 20:11:34
     UNSCRAMBLED, WOBBLE CORRECTED      AVG CT:      23
                                        STD DEV:     41
                                        PEAK CT:    298
                                        TOTAL CTS: 181892
```

```
RAW DATA FROM VL8FILE.DAT;42      FRAME 1, PLANE 7
DATA COLLECTED ON 28-DEC-88 FROM 20:13:39 TO 20:18:32
     UNSCRAMBLED, WOBBLE CORRECTED      AVG CT:       8
                                        STD DEV:      3
                                        PEAK CT:     20
                                        TOTAL CTS: 61955
```

VL8FILE.IMG

DATE
DEC 28, 1988

BEG TIME
19:39:21:27

END TIME
19:44:14:45

DURATION
0: 4:53:18

PEAK CNT
DENSITY
261

PROMPT
CO CNTS
.126E+06

RAW RAND
COUNTS
.111E+03

TOTAL
COR CNTS
.127E+06

FIG. 1(g)

VL8FILE.IMG

DATE
DEC 28, 1988

BEG TIME
20:52:1:23

END TIME
20:56:54:41

DURATION
0: 4:53:18

PEAK CNT
DENSITY
294

PROMPT
CO CNTS
.107E+07

RAW RAND
COUNTS
.743E+06

TOTAL
COR CNTS
.343E+06

FIG. 1(h)

ANTIGEN-SPECIFIC COMPOSITION AND IN VIVO METHODS FOR DETECTING AND LOCALIZING AN ANTIGENIC SITE AND FOR RADIOTHERAPY

TECHNICAL FIELD

This invention relates to a unique use of a positron-emitting radionuclide such as Iodine-124 for labelling antigen-specific antibodies and its application to the detection and localization of specific antigenic sites as well as for radiotherapy of tumors associated with the antigenic sites.

BACKGROUND ART

Previous work with radioactivity for diagnosis and therapy of human tumors was focused on the use of by-product sources of radioactivity such as Iodine-131, Y-90 and the like. These are reactor-produced radionuclides.

Tumor specific monoclonal antibodies have been used extensively in nuclear medicine to carry radioactivity to tumors for what will ultimately be a therapeutic and diagnostic purpose. (Larson, Radiology 165:297-304, (1987)). Therapeutic responses have been reported in melanoma (Larson, Radiology 155:487-492, (1985)); lymphomas (Early et al, JNM 28:692 (1987)); Zimmer et al: JNM 28:603, (1987)); hepatomas (Ettinger et al, Cancer Treat Rep 66:289-297, (1982)), using intravenously injected radiolabeled anti-tumor antibodies as the sole modality of therapy. Intracavitary therapy has been applied successfully in ovarian cancer (intraperitoneal injection), as well as pericardium and pleural spaces. (Epenetos, Lancet pp. 1441-1443, (1984)).

At present, the vast majority of studies are being performed using both diagnostic and therapeutic by-product radioactive material. This involves principally beta decay, or internal conversion radionuclidic decay. Iodine-131 is the most common antibody radiolabel, but Indium-111, Ga-67, Tc-99m, Cu-64, and Y-90 have also been widely used. In addition, promising work has been proposed with the alpha-emitters, Bi-212 and Pb212. (Kozak et al, Proc Natl Sci 83:474-476, (1986)).

Recently, investigators have begun to explore positron labeled antibodies because of the superior imaging properties of PET, and the possibility that such radiopharmaceuticals may become useful diagnostic reagents. Recent reports have involved the use of Ga-68 (68 minutes) and F-18, (110 minute half-life) (Otsuka et al; JNM 28:282, 1987) I-124 (4.2 day half-life) (Miraldi, JNM 28:1078, (1987)); and Zr-89 (78 hour half-life) (Eary et al, JNM 27:983, (1986)).

Positron Emission Tomograph offers quantitative abilities that are unique in nuclear medicine in that the concentration of radioactivity can be determined in depth of tissue without interference from radioactivity in surrounding or overlying tissue. This quantitative tomographic imaging is based on the unique physics of positron decay. Also, positron-emitting radionuclides of C-11, 0-15, and F-18, can be readily incorporated into a variety of biomolecules that are excellent in vivo tracers as can be seen in Table 1.

TABLE 1

Positron Emitting Radionuclides Commonly Used as Radiotracers in Biology

| Radionuclide | Half-life | Example of Use |
|---|---|---|
| O-15 | 124 s | Blood flow |
| N-13 | 10. min. | Amino acid tracer |
| C-11 | 20.3 min. | dopamine analogue |
| F-18 | 110 min. | glucose analogue |

Quantitative imaging of several biologically relevant radiotracers has lead to methods for estimating important biochemical processes non-invasively in vivo: including regional cerebral glucose metabolism (Reivich et al: Circ Res 44:127-137, 1979); blood flow, oxygen extraction and oxygen utilization; (Frackowiak et al JCAT 4:1448-1452, 1980); and dopamine receptor concentration, (Wong et al: Science 234:1558-1563, 1986; Wong et al Science 226:1393-1386, 1984), as examples. The radionuclides of relevance to antibody labeling are of various half-lives, and a partial listing is seen in Table 2 below.

TABLE 2

Positron Emitting Radionuclides of Relevance to Radiolabelling of Monoclonal Antibodies. (Data from Dillman, MIRD Pamphlet 10, Society of Nuclear Medicine Publishers, New York, 1975)

| Radionuclide | Positron %^ | Decay Energy* | Half-life | Equilibrium Absorbed Dose Constant** |
|---|---|---|---|---|
| Ga-68 | 89 | .8340 | 1.13 hours | 1.5742 |
| F-18 | 97 | .3942 | 1.83 hours | .5157 |
| Se-73 | 65 | .5664 | 7.20 hours | .8406 |
| Ga-66 | 56 | 1.8989 | 9.3 hours | 2.389 |
| Cu-64 | 19 | .2794 | 12.8 hours | .2799 |
| Co-55 | 81 | 1.5 | 18.2 hours | — |
| As-72 | 17 | 2.5 | 26 hours | — |
| Zr-89 | 22 | .90 | 78.4 hours | — |
| I-124# | 25 | .9818 | 101. hours | .4578 |
| As-74 | 29 | .5664 | 430 hours | .5695 |

^ % includes all positrons, even when multiple, per decay
*energy of most abundant positron
**gm-rad/microcurie-hour, summed for all particulate energy including low energy x-ray less than 10 kev. (non-penetrating radiation)
Production example: 124-Te(p, n)I-124, 13 Mev protons, requiring 170 mg Te-124 target; yield = 176 micro-curie/microAmp-hour
^^ Production example: 66-Zn(p, n)Ga-66, estimated production of approximately 200 microcuries/microAmp-hour, 66-ZnO as the target material.

Because these biologically relevant positron emitting radionuclides are short-lived a cyclotron for the production of the radionuclides must be near-by to the clinics where the radioisotopic preparation is injected in vivo. The imaging devices presently in use are highly developmental in nature and complex. There is a need for specialized personnel to operate and maintain the cyclotron, PET scanners and associated computer equipment necessary for image interpretation.

The elegant and unique information obtained with these methods, has led to the proliferation of PET/Cyclotron centers with both radionuclide production and quantitative imaging capability. At present there are 26 centers in the U.S., and 60 in hospitals worldwide. By 1995, it has been estimated that 300 PET/Cyclotron facilities will be in place, most likely related to the unique research opportunities which this machine offers.

In addition to cyclotrons as a source of positron emitters, there are several radiopharmaceuticals that can be produced from a "generator" system, of suitable quality to provide easily accessible radionuclide on a continual basis, in the same way that the ubiquitous Tc-99m is produced on-site for standard nuclear medicine procedures by eluting a column that contains the radioactive parent isotope, MO-99. A list of positron emitters available from generator systems is shown in Table 3 below.

TABLE 3

Positron Emitting Radionuclides Available from Generator Systems (CRC Press Radiotracers for Medical Applications II: Columbetti Chapter 4 p. 133–168)

| Daughter (half-life) | Parent (half-life) | Separation System | |
|---|---|---|---|
| | | Column | Eluant |
| Ga-68 (1.12 h) | Ga-68 (280 d) | Alumina | .005M EDTA |
| Rb-32 (1.3 min) | Sr-82 (25 d) | BioRex70 | .3M Acetate |
| Sc-44 (3.9 h) | Ti-44 (46 y) | Doxex 1 × 8 | .2M HCl |
| I-122 (3.6 m) | Xe-122 (20 h) | — | — |
| As-72 (26 h) | Se-72 (8.4 d) | — | — |

The periodic table is divided roughly in half into those elements which are neutron rich, and those which are neutron poor. Neutron rich elements (produced in a reactor) decay by competition between beta-minus decay and internal conversion, where-as neutron poor elements (cyclotron produced), decay by positron emission, and in some cases electron capture.

For reasons that are mainly historical, principally related to the greater weapons and power applications of reactors, medical applications of radioisotopes which are produced as a part of this procedure (by-product material) are much more wide spread. This includes therapy applications, in which radionuclides such as I-131, Au-198, P-32 and Y-90 have been used.

In general reactors are placed in remote areas, away from population centers, because the by-product material which is produced as a natural part of the operation of these machines, contains large quantities of long-lived radioactive elements that have the potential for contaminating the environment. Thus medically useful radionuclides that are useful for nuclear medicine applications must have relatively long half-lives or be available in a generator form that can be shipped long distances.

Instead, cyclotrons (accelerators), have been used principally for "atom-smashing" experiments, and have had a major role in the current understanding of the state of matter, and basic physical principles that underlie the universe. And yet they are the most versatile of radionuclide production systems, particularly for positron emitters.

In principle, positron emitting isotopes should be equally applicable to therapeutic applications, as beta minus emitting radionuclides. The availability of cyclotrons on site in many hospitals, provides for the convenient production of positron emitting radionuclides with a range of half-lives, some of which are far too short to be shipped conveniently.

This ability to use a range of half-lives in the therapy of human tumors with radiolabeled anti-tumor antibodies, is a considerable advantage because the biology of a particular targeting situation varies widely, and with it the optimal half-life that will lead to the best therapeutic index, in terms of the ratio of Rad dose to tumor and normal tissue, in terms of Rad dose.

Beta decay and positron decay (sometimes called beta-plus decay) is accompanied by the emission of a neutrino, which carries off angular momentum and some of the energy of the transition. In fact, there are a spectrum of energies for both particles, that accompany a single decay, and the amount of energy is usually described as the mean energy, which is about ⅓ of the maximum energy that the beta plus or minus particle may have. It is this energy of decay which determines how far the decay particle travels in tissue, and how much energy is deposited in the tissue.

For all practical purposes, beta minus and beta plus decay at the same energy of emitted particles, deliver very nearly identical amounts of radiation to the tissues. When the beta minus comes to rest in tissue, it is usually captured in the electron cloud of a nearby atom, but the positron combines with an electron, and annihilates, with the production of two gamma photons of 511 KeV, that comes off at 180 degrees from one another. Both lose energy in tissue principally by collision with orbital electrons, until they come nearly to rest.

In addition to the above art the following findings were also described in the past. Scheinberg and Strand disclosed a method for high resolution gamma ray imaging of mouse tumors obtained with leukemia cell-specific monoclonal antibodies labelled with bifunctional radioactive metal chelates (Scheinberg, D. A. and Strand, M., Science 215: 1511 (1982)). This reference describes the possibility that labeled tumor-specific antibodies such as those labeled with Iodine-131 may have tumoricidal effects in reference to Orderet al, Cancer Research 40(A)Part 2: 3001 (1980). J.A.M.A. 259 (14): 2126–2131 (1988) is a review article describing current and potential uses of positron emission tomography in clinical medicine and research related to oncology. The article surveys imaging procedures for evaluation of patients with malignant tumors and describes diagnostic tools for assessing the recurrence of malignant tumors after radiation therapy for the study of tumor biology (metabolic studies) and the like. However, no specific mention of positron emitting radiolabels attached to antibodies for the treatment of patients afflicted with tumors is mentioned.

Link et al described the production of Zr-89, a positron emitter, and its evaluation as a protein label (Link, J. M., et al., J. Labeled Comp. Radiopharm. 23(10–12):1297–1298 (1986)). Zr chloride or oxalate are reported to be transchelated non-specifically to plasma protein to which they bind weakly. In addition, the excretion pattern of Zr-DTPA injected into animals is discussed. However, no mention is made in this reference of any therapeutic use of positron emitting labels for therapeutic uses.

U.S. Pat. Nos. 4,331,647, 4,361,544, 4,444,744, 4,460,561 and 4,460,559 to Goldenberg all utilize radiolabels such as alpha-emitters, beta-emitters or positron-emitters in general for tumor radiotherapy. These patents are all somewhat related to one another and claim from broad methods of tumor radiotherapy encompassing the injection of radiolabeled antibody which is specific to a marker (U.S. Pat. No. 4,361,544) to more limited methods of tumor radiotherapy comprising the peritoneal injection of the radiolabeled antibody followed with radiation of thermoneutrons directed to the tumor location (U.S. Pat. No. 4,361,544), a method of tumor radiotherapy comprising the peritoneal injection step described above, locating a tumor with a photoscanning device and the irradiation of the tumor locus with thermoneutrons (U.S. Pat. No. 4,444,744), to a method of tumor radiotherapy comprising the described peritoneal injection, the further injection of an indifferent immunoglobulin carrying a different radiolabel, localizing the tumor by photoscanning the indifferent immunoglobulin label and finally irradiating the tumor with thermoneutrons. Some radiolabeled antibodies also are required to carry a Boron-10 isotope. The antibodies may be monoclonals, polyclonals or fragments thereof. However, no use of I-124 radiolabeled antibodies is mentioned.

U.S. Pat. No. 4,454,106 to Gansow et al describes therapeutic and diagnostic methods utilizing metal chelate-labeled monoclonal antibodies. The metals employed are alpha-emitters, beta-emitters or Auger electron-emitting isotopes. The diagnostic techniques utilize positron-emitting metals as well as fluorogenic or paramagnetic metals. More specifically, Gansow et al claim a method of treating cellular disorders comprising administering to a patient monoclonal antibodies labelled with a chelate of a radiometals such as Ga-68 and Co-55, but neither Iodine-124 nor other positron emitters.

U.S. Pat. No. 4,737,579 to Hellstrom et al discloses novel monoclonal antibodies to human non-small cell lung carcinomas (NSCLS) displaying a high degree of binding to tumor cells. These antibodies are utilized in diagnostic methods, particularly suitable for the determination of the presence of a malignant condition in a patient. These antibodies are radiolabeled with "a label capable of producing a detectable signal" (see, claim 3) and gamma-emitters are apparently intended because there is a reference to imaging by means of a gamma camera (see, column 7, line 57). No mention is made in this patent however to either therapeutic uses or to the utilization of positron emitters.

U.S. Pat. No. 4,735,210 to Goldenberg relates to a lymphographic organ imaging method which requires the subtraction of a negative image produced using a gross imaging agent from a positive image produced with a specific antibody imaging agent. This is the latest of the Goldenberg patents and it seems to encompass only radiocolloids with a radiolabel such as Tc-99, Au-198, Hg-197, In-111, Ru-97, Ga-67, I-131 or I-123 and the like. Other elements are also called for in claims 12 and 13 of the patent. No mention again is there to therapeutic uses.

U.S. Pat. No. 4,466,951 to Pittman describes a primary amine-containing therapeutic or tracer agent which is prepared by binding cellobiose to the tracer agent to render it non-metabolizable and then binding an antibody to it to provide the capability of introducing the therapeutic or tracer agent into a cell. The therapeutic or tracer agent may contain Boron-10 and also be labeled with a radioisotope, preferably chelated to the primary amine. Radioisotopes such as I-131, I-125 and I-115 are utilized but I-124 is not mentioned (see, column 8, line 67 and column 11).

U.S. Pat. No. 4,659,839 to Nicolotti et, al describes a coupling agent for joining a paramagnetic or radionuclide metal with an antibody fragment by means of a chemical linking group (see, claim 1). The metal ion can be I-125 as well as a variety of paramagnetic ions (column 7, lines 30–46). Positron-emitting radionuclides are mentioned (see, line 45 of column 7) but not in the context of therapeutic uses.

Thus, the need still exists for better detecting and therapeutic methods specifically targeting antigens such as those associated with tumors which afford a greater accuracy and highly successful results.

DISCLOSURE OF THE INVENTION

This invention relates to an antigen-specific composition, comprising
an antigen-specific antibody or antigen-binding fragment thereof labeled with Iodine-124 at a site other than and which does not significantly interfere with the antibody-antigen binding site.

In addition, this invention also relates to an in vivo method of radiotherapy directed to a localized antigenic site comprising administering to a subject in need of such therapy an amount of the antigen-specific composition described above which is effective to attain a desired effect.

Still another part of this invention is an in vivo method for detecting and localizing an antigenic site in a subject in need of such detection, which comprises
administering to the subject an amount of the antigen-specific composition described above which is effective to localize the antigen-antibody binding site with the aid of a I-124 detector; and
scanning the subject's body with the detector to attain the localization of the site.

In still another facet of the invention it is disclosed and in situ method of radiotherapy directed to a localized antigenic site in a subject in need of such therapy, which comprises
administering to the subject an amount of the antigen-specific composition described above which is effective to localize the antigen-antibody binding site;
scanning the subject's body with a I-124 detector to attain the localization of the site; and
in situ delivering a positron-emitting labeled antibody chelate, said chelate being capable of binding to either the I-124 antibody or fragment thereof, or the antigen at a site other than the antibody-antigen binding site.

BRIEF DESCRIPTION OF THE DRAWINGS

A more complete appreciation of the invention and many of the attendant advantages thereof will be readily perceived as the same becomes better understood by reference to the following detailed description when considered in connection with the accompanying figures.

FIG. 1(g) is a reconstruction of sinogram (a), 0.025 mCi of I-124 alone, with standard random coincidence and deadtime corrections. Detector inhomogeneity correction omitted.

Figure 1A:
FIG. 1(a) is a sinogram of a point source of 0.025 mCi of I-124 totally within the plane; no I-131 present.
Figure 1B:
FIG. 1(b) is a sinogram of the same 0.025 mCi I-124 source with a point source of 0.61 mCi of I-131 5cm out of the plane (inferior). There was no observable effect from the I-131.
Figure 1C:
FIG. 1(c) is a sinogram of the same 0.025 mCi I-124 source with a point source of 0.61 mCi of I-131 totally within the same plane (I-131/I-124 ratio approximately 24:1). The I-124 is clearly visible against a slightly increased "background". Comparison with (d), a sinogram of the 0.61 mCi I-131 source alone, shows that the uncorrected count rate from the I-124 component has been decreased very slightly due to the higher singles rate, but it is anticipated that an appropriate random coincidence and deadtime correction would compensate for this.
Figure 1D:
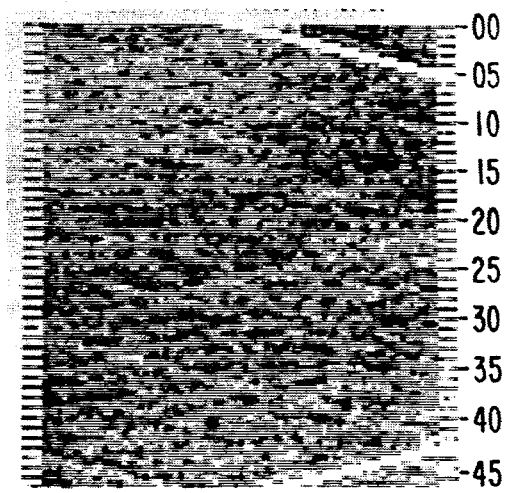
FIG. 1(d) is a sinogram of 0.61 mCi I-131 source alone; no I-124 present. The effects of the I-131 are distributed fairly uniformly in spite of the source being a single point. Thus it should be possible to subtract out these effects provided that the I-131 does not fill the entire field of view (an unlikely situation).
Figure 1E:
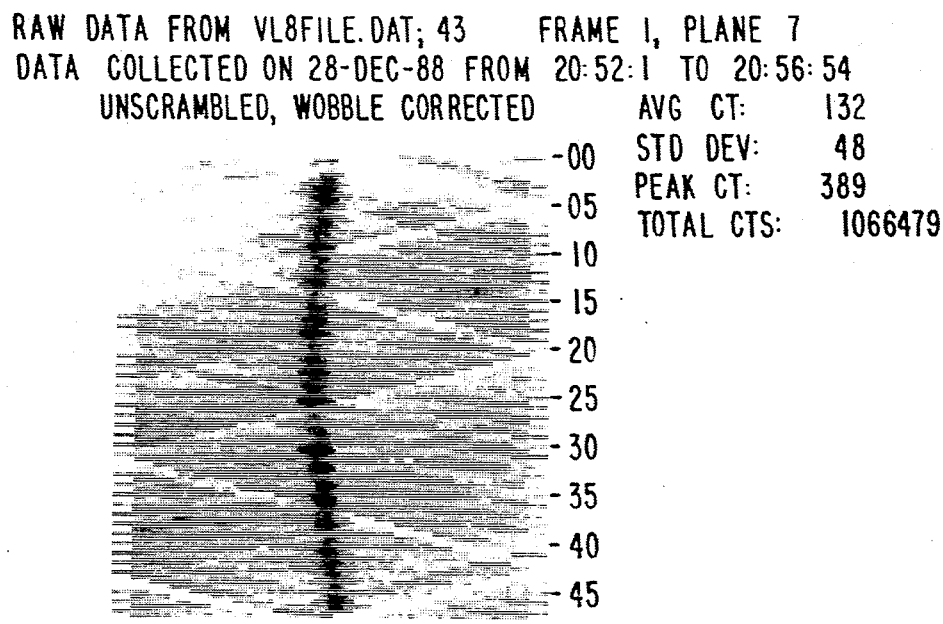
FIG. 1(e) is a sinogram of 0.025 mCi I-124 source with a point source of 2.7 mCi I-131 totally within the same plane (I-131/I-124 ratio approximately 108:1). The I-124 is still clearly visible but the "background" is more significant. Subtracting this "background" (f) shows that the uncorrected count rate from the I-124 component has been decreased significantly (to approximately one half) due to random coincidence and deadtime effects. Applying standard corrections based on "conventional" positron emitters with few single gamma rays present, may prove to be adequate, but with a correction factor of this magnitude, further investigation is necessary.
Figure 1F:
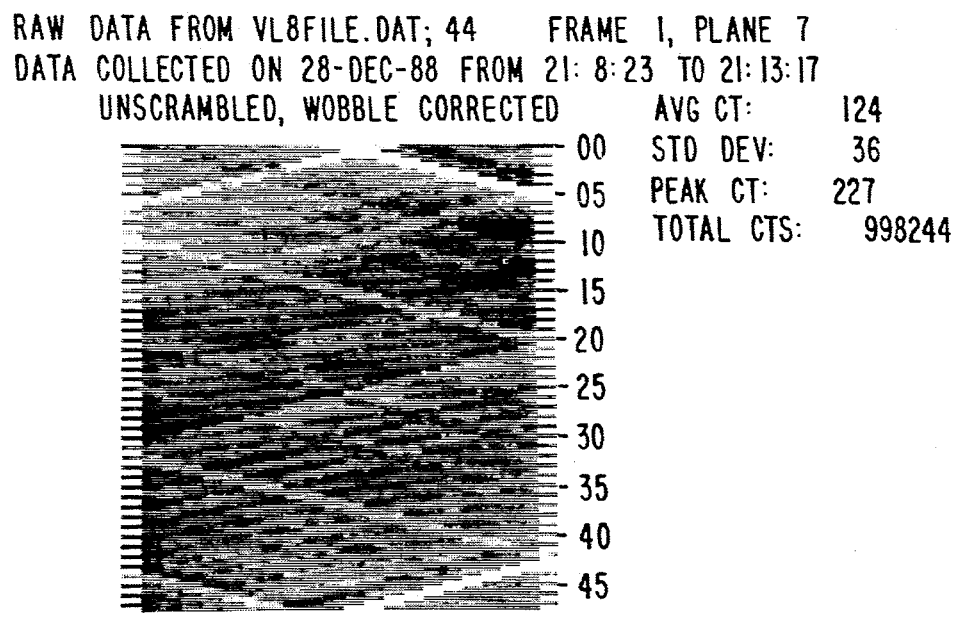
FIG. 1(f) is a sinogram of 2.7 mCi I-131 source alone.

(h) Reconstruction of sinogram (e) 0.025 mCi of I-124 in the presence of 2.7 mCi of I-131, with standard random coincidence and deadtime corrections. "Background" has not been subtracted. Detector inhomogeneity correction omitted.

Other objects, advantages and features of the present invention will become apparent to those skilled in the art from the following discussion.

BEST MODE FOR CARRYING OUT THE INVENTION

This invention arose from a desire by the inventors to improve on prior art technology directed to the detection and localization of antigenic sites such as antigenic tumor sites as well as directed to antigen-specific radiotherapy with particular application to antigen-associated tumors or cancers.

Positron emitters labeled to anti-tumor antibodies have the potential for improved radiotherapy, inter alia, because of the following two main advantages.

(1) Dosimetry is markedly improved due to the quantitative nature of PET imaging of in vivo radioisotope distributions.

(2) The choice of half-life and radionuclide species which make it easier to optimize the chemistry of linkage, and to optimize the therapeutic index between tumor and radiosensitive normal tissue, based on in vivo kinetics of antibody targeting to tumor.

Although in the past it has been recognized that antibodies can be labeled with positron-emitting radionuclides no prior report has existed as to any utilization of Iodine-124 for clinical uses such as in therapy or in the detection of tumors. In comparison to by-product labels and other positron emitters the use of Iodine-124 results in improved dosimetry for normal tissues and tumors as well as in improved detection even in the presence of other radiolabels such as Iodine-131.

The present invention is a unique use of a positron-emitting radionuclide labeled to an antigen-specific antibody or fragment thereof which utilizes the binding capability of the antigen for detection and therapeutic purposes. Of particular importance is the application of the present technology for the detection and/or therapeutic administration to cancer patients.

The antigens to which the antibodies utilized in this invention have specificity are tumor-associated antigens or markers for tumor cells. These markers may be substances elaborated by the tumor cell or be part of the cell itself. The marker may be present on the outside of the cell or it may be intracellular and be present in any of the various parts present inside the cell. As a mere exemplary list the following markers are considered encompassed within the confines of this invention. These include oncofetal antigens, placental antigens, oncogenic or tumor virus-associated antigens, tissue associated antigens, organ associated antigens, ectopic hormones and normal antigens or variants thereof. Occasionally, a sub-unit of a tumor-associated marker is advantageously used to raise antibodies having higher tumor-specificity, e.g., the beta-subunit of human chorionic gonadotropin (HCG), which stimulates the production of antibodies having a greatly reduced cross-reactivity to non-tumor substances. Suitable such marker substances to which specific antibodies may be raised which are useful in the present invention include, but are not limited to, alpha-fetoprotein (AFP), human chorionic gonadotropin (HCG) and/or its beta-subunit (HCG-beta), colon specific antigen-p (CSAp), prostatic acid phosphatase, pancreatic oncofetal antigen, placental alkaline phosphatase, pregnancy beta1-globulin, parahormone, calcitonin, tissue polypeptide antigen, T-antigen, beta2-macroglobulin, galactosyl transferase-II(GT-II), gp-52 viral-associated antigen, ovarian cystadenocarcinoma-associated antigen (OCAA), ovarian tumor-specific antigen (OCA), cervical cancer antigens (CA-58, CCA, TA-4), basic fetoprotein (BFP), terminal deoxynucleotidyl transferase (TdT), cytoplasmic melanoma-associated antigens, human astrocytoma-associated antigen (HAAA), common glioma antigen (CGA), glioembryonic antigen (GEA), glial fibrillary acidic protein (GFA), common meningioma antigen (CMA) and tumor angiogenesis factor (TAF), and many others known in the art.

Antigen- or marker-specific antibodies may be obtained by methods which are known in the art and need not be further described herein. In general, an animal such as rabbit, goat or the like is challenged with a tumor-associated antigenic substance and its immune system is allowed to react by producing polyclonal antibodies specific to the marker. The animal is then bled and the immunoglobulin fraction of the blood is then isolated by known techniques such as affinity chromatography and the like (Herberman et al, "Immunodiagnosis of Cancer", Marcel Dekker, Inc., N.Y. (1979)). The specificity of the polyclonal antibodies is limited because they usually contain a small proportion of the antibody population which cross-reacts when non-tumor-associated antigens or markers. Even after sequential purification of the antibodies with different technologies still a portion of the antibody population is still cross-reactive. In spite thereof these polyclonal antibodies are still considered within the present invention to be monospecific to the target antigen.

As is known in the art a more highly monospecific type of antibody is a monoclonal antibody which is obtained by hybridization technology. The antibody produced in this manner is as its name indicates "monoclonal" and requires no further purification to increase its specificity. This type of antibody is a more preferred type than the polyclonal antibody described above. Typically, monoclonal antibodies are obtained by fusing an antibody-producing animal lymphocyte spleen cell with a human, mouse or rat myeloma cell to obtain a hybrid cell. The hybrid cell is then cloned and selected for its ability to produce an antibody specific to the marker with which the animal had been challenged by technology known in the art.

Antibody molecules are one group preferred for the practice of this invention. However, another group of molecules which is also suitable for use herein are fragments of antibodies such as Fab fragments and the like. Any fragment of an antibody which has affinity and specificity for a target antigen is suitable for use herein and is therefore part of still another preferred group for the practice of this invention.

Antibodies and fragments thereof can be radiolabeled by methods known in the art which need not be described herein in much detail. Suitable technology is that disclosed by Wagner et al, Jnucl. Med. 20:428 (1979); Sundberg et al, J. Med. Chem. 17:1304 (1974); Feteanu, "Labeled Antibodies in Biology and Medicine", pp. 214–309, McGraw Hill, N.Y. (1978); Saha et al, J. Nucl. Med. 6:542 (1976). However, other technology is also suitable for the preparation of radiolabeled antibodies or fragments thereof in accordance with this invention.

The amount of iodine with which the antibody or fragment thereof is labeled may be varied. In general, a higher proportion of radiolabel permits a more easy identification and localization of an antigenic site and a more effective radiotherapy for the treatment of tumors. However, in certain instances a lower dose of radiolabel may be preferable such as in the case of the multiple step method disclosed herebelow. Typically, about 1 to 10 Iodine-124 atoms per antibody molecule can be introduced, and more preferably about 1 to 3 iodine-124 atoms per antibody molecule, and still more preferably about 1 to 2 iodine-124 atoms per antibody molecule. However, other proportions are also suitable and are considered to be within the confines of this invention.

In fact, when monoclonal antibodies are utilized because of their higher specificity, a lesser amount of radiolabel is needed to attain an equally efficient localization and high resolution of the scanning image as when polyclonal antibodies are utilized. In order to protect the antibody-antigen binding site the radiolabeling of the antibody or fragment thereof may be conducted in the presence of antigen. Thereafter, the antigen is separated from the antibody and the radiolabeled antibody is readied for use as is known in the art.

In certain instances it may be advantageous to use mixtures of I-124 radiolabeled antibodies or fragments thereof which have specificities for different antigens associated with the same or different tumor or tumor cell types. This approach may enhance the detection and localization or therapy and may also serve for screening of more than one type of tumor associated antigens as well.

In cases where other antibodies are radiolabeled with a different isotope of the same element, such as Iodine-131 and the like they are preferably injected currently with the radiolabeled antigen-specific antibody described above. In this case a reference substance having a molecular species essentially showing the same kinetics of binding, distribution and metabolism as the radiolabeled antigen-specific antibody is utilized. The two may be administered simultaneously, e.g., by injection, and a high resolution is attained as is shown in the examples.

The antibodies of the invention can be administered in various forms of, e.g., injectable compositions. Typically, the antigen-specific composition of the invention comprises an antigen-specific antibody or antigen-binding fragment thereof labeled with Iodine-124 at a site other than, and which does not significantly interfere with, the antibody-antigen binding site. The composition may additionally contain other ingredients such as a pharmaceutically-acceptable vehicle which may be an aqueous solution and the like. Other additives may be a buffer, and other ingredients known in the art for preserving the integrity of polypeptides and the like. The administration of the composition may be intravenous, intradural, intrathecal or intra-lymphatic, among others. The composition may be administered into an artery, vein, lymphatic system or spinal fluid over the course of about 1 to 60 minutes, and preferably of about 15 to 30 minutes. In particular situations, one route is preferable over others. For example, when a lymphatic tumor is to be detected and/or treated, intra-lymphatic administration is preferable. Also, when the antigen is associated with a peritoneal tumor, intraperitoneal administration is indicated. In other situations intradermal and/or intracavitary administration may be advantageous for tumors restricted to areas which are closed to particular regions of the skin and/or body cavities. This, in addition to delivering more of the composition to the site precludes the general distribution of the composition throughout the subject's body and consequently lowers the chances for any detrimental side-effects.

In another aspect of the invention it is provided herein an in vivo method of radiotherapy directed to a localized antigenic site which comprises administering to a subject in need of such therapy an amount of the antigen-specific composition of the invention which is effective to attain a desired effect. In general, a reduction in the size of a tumor associated with the antigenic site can be attained by the administration of one or more doses of the composition of the invention. Typically, the composition of the invention comprises about 1 to 1000 mg of the antigen-specific radiolabeled antibody per ml of solution, preferably about 1 to 500 mg of radiolabeled antigen-specific antibody per ml of solution, and still more preferably about 5 to 50 mg of radiolabeled antigen-specific antibody or fragment thereof per ml of solution. Typically, the solution is adjusted to a pH of about 5.5 to 8.5, more preferably about 6 to 7.5, and still more preferably about pH 7 with a pharmaceutically acceptable buffer as is known in the art. This solution may also contain saline in order to be ionically equilibrated with the subject's blood and other pharmaceutically acceptable additives as is known in the art. For each type of administration a pharmaceutically-acceptable vehicle may also be utilized, many of which are known in the art.

In one embodiment of the method of the invention the composition is administered by injection. As indicated above, when the antigen or antigen-associated tumor is localized in a specific area a particularly suitable route is utilized. By means of example, if a lymphatic tumor is to be treated and/or detected, the composition is administered by intra-lymphatic injection. In the case of a tumor being localized in a body cavity, intracavitary administration may be indicated. When a tumor is located under the skin, intradermal administration may be the most appropriate. Also, when the antigen or tumor are lodged in the peritoneal cavity the composition may be administered intraperitoneally.

Also part of this invention is an in vivo method for detecting and localizing and antigenic site in a subject in need of such detection, the method comprising administering to the subject an amount of the antigen-specific composition of this invention which is effective to localize the antigen-antibody binding site; and scanning the subject's body with a radiolabel detector to attain the localization of the site.

Methods and apparatus for scanning a subject's body which contain a radiolabeled antibody or fragment thereof, e.g., positron-emitting radiolabels, are known in the art and need not be further described herein.

Also provided herein is an in situ method of radiotherapy directed to a localized antigenic site in a subject in need of such therapy, which method comprises administering to the subject an amount of the antigen-specific composition of this invention which is effective to localize the antigen-antibody binding site;

scanning the subject's body with a radiolabel detector to attain the localization of the site; and thereafter in situ delivering a positron-emitting labeled antibody chelate, said chelate being capable of specifically binding to either the antibody or fragment thereof or the antigen at a site other than the antibody-antigen binding site.

Any antibody which exhibits cell-binding or antigen-binding capability at the cell targeted for therapy and/or detection and localization can be employed. Fragments of antigen-specific antibodies are also suitable for use herein. Most preferred are monoclonal antibodies or fragments thereof which have specificity and affinity for a specific antigenic site.

Methods for the preparation of the positron-emitting radiolabeled antibody chelate are known in the art and need not be described in detail herein. In general, the chelate conjugated to an antibody is a positron-emitting metal atom such as Ga-66 chelate bonded to an amine group which serves to link the positron emitting chelate to the antibody. By reacting the derivative with the antibody a chelate conjugated antibody is obtained which is then reacted with a positron-emitting metal salt to produce the metal chelate conjugated antibody. The thus obtained metal-containing conjugate can then be further purified by means of, e.g., a sizing column, and one or more ion-exchange resins until the positron-emitting radionucleide label is highly complexed in the chelate. Typically, greater than about 80% of the positron-emitting label is chelated in the conjugate, and more preferably greater than about 90% and still more preferably at least about 95% of the antibody activity and specificity is retained by the conjugate.

The second type of antibodies utilized in the chelate are raised to a different epitope of the antigenic site, e.g., tumor antigen or to a different antigen with which the tumor is associated. Thus, once administered to the subject, the chelate is allowed to concentrate in the targeted area. The therapeutic and/or detecting and localizing effect occurs when the conjugates are near or in contact with and bind to the targeted cells. Cell attrition or death is believed to be a direct or indirect result of the positron-emitting labeled antibody chelate being in proximity with the targeted cell.

As already indicated above, a plurality of benefits accrue from this type of method. The high specificity of the conjugated antibody helps minimize total radiation dosage since only enough radiation for attack on the targeted cell need to be employed. Moreover, positron-emitting labeled antibody chelates are generally cleared rapidly from the body if the conjugated antibody is disrupted. Thus, the isotope may be short-lived and the affinity constant by which the isotope is retained in the longer antibody chelate is very high resulting in a stable bound positron-emitting label. Furthermore, since the amount of radiation employed is minimized, the radiation hazard to the persons involved in the preparation and administration of the treatment is significantly reduced as well. Also, the tissue damage or whole body dose during therapy, particularly during repeated therapy, are markedly reduced when compared with other methods of radiation therapy such as isotope implants, external radiation therapy and immunotherapy employing Iodine-131 labeled antibodies.

Accordingly, the present methods are antigen-specific, require lower radioactive doses and are able to reach not only the original antigen-containing cells but also cells which are metastasized. This capability of reaching metastasized cells in places unknown to the therapist is also unique and singularly useful for cancer therapy.

In a preferred embodiment the positron-emitting radiolabeled antibody chelate is administered by injection, and more preferably by localized injection such as intra-lymphatic, intra-dermal, intra-cavitary, intraperitoneal and the like, when the tumors are lodged in the lymphatic system, under the skin, in a body cavity and in the peritoneum, respectively.

In general, the dose of I-124 administered for radiotherapy is substantially higher than the one used for localization of cancerous areas. The I-124 radiolabel is preferably administered in an amount of about 0.03 to 4 mCi per Kg. weight per dose, and more preferably about 0.1 to 2 mCi per Kg weight per dose. The higher portion of the range is typically utilized for radiotherapy whereas the lower portion is mostly utilized for detecting purposes. The doses may typically be spaced at intervals from about 1 to 7 days to about 3 to 8 weeks and sometimes longer periods.

Having now generally described this invention, the same will be better understood by reference to certain specific examples, which are included herein for purposes of illustration only and are not intended to be limiting of the invention or any embodiment thereof, unless so specified.

EXAMPLES

Example 1

Intravenous injection of I-131 Fab fragments for therapy of Metastatic Melanoma

Intravenously injected monoclonal antibodies against the p97 antigen of melanoma have resulted in good localization, especially with regard to the Fab fragments of the antibody, 96.5. This Fab, is rapidly cleared into the tumor and is relatively tumor specific, although at lower doses (mg amounts of the Fab fragment) there is also considerable uptake in the liver.

Dosimetry estimates using I-131 Fab have been made for normal tissues based on the measured characteristics of uptake in a series of patients with melanoma (33 studies in 22 patients). The resulting information has been determined as follows.

Whole body clearance: 33 hours.
Tumor clearance: 45 hours.
Liver clearance: 20 hours.

The route of clearance is through the kidneys. This leads to an estimate of bladder dosimetry of 0.16 hours which is based on commonly employed estimates for a non-concentrated radiopharmaceutical cleared through the kidney using standard MIRD approaches and S-values available in standard tables (Larson et al, JCI 72: 2101-2114 (1983)).

Example 2

Use of I-124 labeled Fab Fragments in accordance with the Invention

Using these same estimates positron-emitter I-124 was evaluated for dosimetry to determine its use as a radiotracer for monoclonal antibody labelling. The results are described in Table 4 below.

There is a comparable exposure to normal tissues, although the results are slightly higher on a per mCi basis.

TABLE 4

COMPARISON OF DOSIMETRY FOR I-131 and I-124 FAB FRAGMENTS: NORMAL TISSUES(JCI 72:2101-2114, 1983)

| Radionuclide Source organ | uCi-hrs/ | Target Tissues ||||| 
|---|---|---|---|---|---|---|
| | | Marrow | Liver | Bladder | Ovary | Whole Body |
| I-131 | | | | | | |
| liver | 1023620 | 0.000003 | 0.0003 | 0.000001 | 0.000001 | 1.10E-05 |
| whole body | 2232592 | 0.000011 | 0.000011 | 0.000011 | 0.000011 | 1.00E-05 |
| blood | 234017 | 0.000011 | 0.000011 | 0.000011 | 0.000011 | 1.00E-05 |
| bladder | 160923 | 0.000004 | 0.000001 | 0.0012 | 0.000019 | 6.00E-06 |
| kidney | 18698 | 0.000007 | 0.000011 | 0.000006 | 0.000003 | 1.10E-05 |
| | Rad | 31.31253 | 334.5853 | 221.3761 | 31.27742 | 37.09712 |
| I124 | | | | | | |
| liver | 948421 | 0.000008 | 0.00046 | 0.000002 | 0.000003 | 2.00E-05 |
| whole body | 2020736 | 0.00002 | 0.00002 | 0.000021 | 0.000021 | 1.30E-05 |
| blood | 212215 | 0.00002 | 0.00002 | 0.000021 | 0.000021 | 1.80E-05 |
| bladder | 145229 | 0.00001 | 0.000002 | 0.0013 | 0.000048 | 2.10E-05 |
| kidney | 16944 | 0.000019 | 0.00003 | 0.000003 | 0.00001 | 2.00E-05 |
| | Rad | 54.02061 | 481.7895 | 310.6346 | 57.63640 | 62.55022 |

Based on the data obtained with I-131 Fab (anti-p97) it is estimated that target to background ratios of 25:1 are achieved between tumor and liver by about 1 week after injection. When a second site on the antibody or an antigenic site is established to bind the positron labeled antibody chelate rapidly, uptake onto the tumor ensues that is relatively rapid with the result that a comparable % of the injected dose is retained in the tumor as would be retained in the primary targeting. This method has the net effect of dramatically reducing the background, since even when whole IgG is used, the unreacted antibody can be first removed from the blood and other non-tumor tissue sites by a variety of scavenging methods

Example 3

Comparative administration of I-124 and I-131

A comparison of the tumor doses for I-131 and I-124 for 3 cases from experiments that have been published are summarized in Table 5 below.

TABLE 5

COMPARISON OF I-24 (POSITRON EMITTERS) TO I-131 for TUMOR DOSIMETRY (Estimated, for non-penetrating radiation) per 100 mCi injected radioactivity.*

| | g-rad/ m-h | Case 1 ||| Case 2 ||| Case 3 |||
|---|---|---|---|---|---|---|---|---|---|---|
| | | A (mic) | T½ Eff | Dose (Rad) | A (mic) | T½ Eff | Dose (Rad) | A (mic) | T½ Eff | Dose (Rad) |
| I-131 | .4164 | 189 | 74 hr.s | 8394 | 40 | 36 hr.s | 1040 | 147 | 36 hrs. | 3201 |
| I-124 | .4578 | 189 | 60 hr.s | 6854 | 40 | 31 hr.s | 902 | 147 | 31 hrs. | 3016 |

Case 1:
(Larson, et al: JNM 27:1021, 1986): Based on the IP injection of I-131 B72.3 with surgical confirmation of concentrations. Patient had peritoneal carcinomatosis due to appendiceal primary carcinoma. The dose given was a tracer level dose of 10 mCi's so response was not monitored. A — amt in tumor in microcuries; T½ Eff — effective half-time of clearance from tumor; g-rad/m-h — absorbed dose constant for non-penetrating radiation.
Case 2:
(Larson, et al: JCI 72:2101-2114, 1983): Based on estimated uptake after iv injection of I-131 anti-p97, Fab, an anti-melanoma. Lesion was localized in the liver, and was of about 450 grams. No tumor response with 135 mCi's injected. Largest single dose was 90 mCi (estimated tumor dose of 936 Rad.
Case 3:
(Larson, et al: Radiology 155:487-492, 1985); Based on estimated uptake measured using a thyroid probe, and from the measured size of tumor involved lymph node at the bifurcation of the inferior vena cava. Definite response observed which lasted 4 months. Total dose from 374 mCi I-131 48.7 Fab (anti-HMW) was computed to be 12000 Rad.
*Computed doses were obtained from using the equilibrium dose constant for non-penetrating radiation for the internally contained radioactivity only for cases 1 and 3, but for case 2, since the tumor was in the liver, and the liver had concentrated a considerable amount of radioactivity, we used the exposure to the tumor from the liver and whole body, assuming the approximate S-values of liver to kidney, since the total kidney was about the same weight, and in a similiar relationship to the liver. 10-15% of the dose to tumor was from external radiation in this instance. (S-values from MIRD Pamphlet #11, Society of Nuclear Medicine Press, October, 1975).

Example 4

Intraperitoneal Injection of Radiolabelled Antibodies for Therapy of Peritoneal Adenocarcinomatosis Excellent targeting of the monoclonal antibody B72.3 has been found after direct intra-peritoneal injection into patients with diffuse peritoneal involvement with adenocarcinoma: colon and small intestine primaries. These studies have yielded the following kinetics.

(1) The uptake into tumor is very rapid.

(2) Once bound to tumor the radiolabeled antibody clears with a t½ of 120 hrs.

(3) Unbound clears from the peritoneum with a t½ of 29 hours.

(4) The whole body clearance is 72 hours.

(5) Renal transit time is 0.16 hours.

(6) Bladder emptying is once every 4 hours.

Peritoneal S values are presently being computed.

Based on surgical studies in these patients the concentration of antibody localized in the tumor was 0.184% of the injected dose per gram. Preliminary studies in humans have determined that the clearance from the tumor is slow, its t½ being about 120 hr. Table 4 above lists the Rad dose deposited in the tumor for 100 mCi injected radioactivity based on available nuclear parameters, the known half-life of the radionuclide and the assumed concentration of I-131 B72.3 antibody, and clearance data for a variety of positron emitting radionuclides (See, Table 5 above).

Example 5

Intralymphatic Injection of Radiolabelled Antibody

Targeting of radiolabeled antibody by intralymphatic route has been successfully accomplished using In-111, T-101 and there is good information on the kinetics of uptake (Carrasquillo et al, New England J. Med. 315: 673-680 (1986)). The targeting to the nodes of the pelvis is virtually instantaneous, and with direct tissue sampling of the lymph nodes, the uptake is very high, being measured at 2.5% of the injected dose per gram. It is practical to deliver radiotherapy using the appropriately chelated metal ion to the retroperitoneal lymph nodes. A comparison of various positron emitting radionuclides for the targeting of lymph-nodes under these conditions is shown in Table 6 below.

TABLE 6

Comparison of the Dosimetry to Lymph nodes and Marrow after IL injection, using radiolabelled T-101, as a comparison.

| Nuclide | Lymph Node | | | Leg | | | Marrow | |
|---|---|---|---|---|---|---|---|---|
| | g-rad/m-h | T½ eff | A (mic) | A (mic) | T½ eff | | S(ut-m*) | A (mic-source) |
| F-18 | 0.5517 | 1.806 | 2500 | 100 | 1.703 | | 0.00002 | 8.50E + 04 |
| | | | Rad 3586.932 | Rad | 135.2944 | Rad | | 4.42E + 00 |
| Ga-68 | 1.5742 | 1.1199 | 2500 | 100 | 1.08 | | 0.00002 | 8.50E + 04 |
| | | | Rad 6346.607 | Rad | 244.3195 | Rad | | 4.42E + 00 |
| Ga-66 | 2.389 | 8.636 | 250 | 10 | 6.69 | | 0.00002 | 8.50E + 03 |
| | | | Rad 7444.506 | Rad | 230.1467 | Rad | | 4.42E + 01 |

*Dosimetry calculations are based on the assumptions of measured clearance from the nodes of approximately 5%/day which translates into T-½ of hours. The measured T-½ from the material retained in the leg was about 24 hours. Concentrations were calculated from considering 100 mCi administered for F-13, Ga-68, and 10 mCi Ga-66. Doses for I-124 were not calculated because the Iodines are not retained by these cells, but instead are rapidly metabolized (Carrasquillo et al: J Nuc Med 23:281-287, 1987).

These values were computed based on a estimated t½ clearance of 125 hours (loss of 5% per day).

Example 6

Multi-step targeting of radiolabelled antibody

The use of a sequence of steps to target radiolabeled antibodies, e.g., monoclonal antibody has been demonstrated (Goodwin et al: J. Nuclear Med. 28:722 (1987)). From the standpoint of a short lived positron emitting radionuclides a two-step procedure can be employed, in which the I-124 labeled antibody, e.g., monoclonal antibody, is first allowed to target the tumor site for a period of days until there is a target to background ratio between the tumor and the background that is sufficiently high. A second injection of a radiolabeled antibody chelate is then administered which can rapidly diffuse throughout the tissues of the body to bind to an activated site on the targeted tumor associated monoclonal antibody or the tumor antigen at a site other than the antigen-antibody binding site.

Based on the preliminary data with I-131 Fab (anti-p97) it is estimated that target to background ratios of 25:1 are achieved between tumor and the liver by about 1 week after injection. When a second site on the antibody or antigenic site is established to bind the positron labeled antibody chelate rapidly, uptake onto the tumor ensures that is relatively rapid with the result that a comparable % of the injected dose is retained in the tumor when compared with that retained in the primary targeting.

This method has the net effect of reducing background dramatically since even when whole IgG is used the unreacted antibody can be first removed from the blood and other non-tumor tissue sites by a variety of scavenging methods.

Example 7

Illustration of the ability to image I-124 with the PC4600 PET scanner in the presence of various amount of I-131

The data are shown before detector inhomogeneity corrections have been applied.

(a) Sinogram of a point source of 0.025 mCi of I-124 totally within the plane; no I-131 present.

(b) Sinogram of the same 0.025 mCi I-124 source with a point source of 0.61 mCi of I-131 5cm out of the plane (inferior). There was no observable effect from the I-131.

(c) Sinogram of the same 0.025 mCi I-124 source with a point source of 0.61 mCi of I-131 totally within the same plane (I-131/I-124 ratio approximately 24:1). The I-124 is clearly visible against a slightly increased "background". Comparison with (d), a sinogram of the 0.61 mCi I-131 source alone, shows that the uncorrected count rate from the I-124 component has been decreased very slightly due to the higher singles rate, but it is anticipated that an appropriate random coincidence and deadtime correction would compensate for this.

(d) Sinogram of 0.61 mCi I-131 source alone; no I-124 present. The effects of the I-131 are distributed fairly uniformly in spite of the source being a single point. Thus it should be possible to subtract out these effects provided that the I-131 does not fill the entire field of view (an unlikely situation).

(e) Sinogram of 0.025 mCi I-124 source with a point source of 2.7 mCi I-131 totally within the same plane (I-131/I-124 ratio approximately 108:1). The I-124 is still clearly visible but the "background" is more significant. Subtracting this "background" (f) shows that the uncorrected count rate from the I-124 component has been decreased significantly (to approximately one half) due to random coincidence and deadtime effects. Applying standard corrections based on "conventional" positron emitters with few single gamma rays present, may prove to be adequate, but with a correction factor of this magnitude, further investigation is necessary.

(f) Sinogram of 2.7 mCi I-131 source alone.

(g) Reconstruction of sinogram (a), 0.025 mCi of I-124 alone, with standard random coincidence and deadtime corrections. Detector inhomogeneity correction omitted.

(h) Reconstruction of sinogram (e) 0.025 mCi of I-124 in the presence of 2.7 mCi of I-131, with standard random coincidence and deadtime corrections. "Background" has not been subtracted. Detector inhomogeneity correction omitted.

Increasing the energy threshold (a complex task because the number of detectors involved) would reduce the "visible" effects of the I-131, would also reduce the recorded random coincidences and therefore give a statistical improvement over "background" subtraction but would not entirely eliminate the major deadtime effects.

Example 8

I-124, Antibody Dosimetry in the Presence of I-131

Positron emission tomography is useful for both diagnostic imaging of antibodies and particularly for quantitation leading to improved dosimetry during radioimmunotherapy. The positron emitting radionuclide, I-124, has a favorable half-life for radiolabelled antibody studies but because of its complex decay scheme, it has generally been bypassed in favor of other nuclides. Measurements made on a BGO based PET scanner (PC4600) have shown that spatial resolution within the plane was 12 mm (FWHM) with I-124 versus 11 mm with F-18, with similar results in the Z-direction. Measurements using a 20 cm diameter phantom gave accurate quantitation over a wide range of activities. Measurements of I-124 in the presence of 25 times as much I-131 showed no significant degradation in the image or in quantitation. 100 times as much I-131 resulted in a significantly increased "background", but only a slight degradation in the image. With correction for random coincidences and dead time there was only a small error in quantitation. Thus, I-124 can be imaged and quantified satisfactorily, even in the presence of large (therapeutic) amounts of I-131.

Example 9

Ratio of I-124 to I-131 obtained under low Absorption Conditions

Measurements made on a BGO based PET scanner have shown that satisfactory imaging and quantitation can be achieved. Spatial resolution was almost as good with I-124 as with F-18 (12 mm versus 11 mm FWHM). quantitation measurements within a 20 cm diameter phantom gave accurate quantitation over a wide range of activities. Further, it has been shown that I-124 can be imaged in the presence of much larger quantities of I-131 with only slight degradation in image quality or quantitation accuracy. The ratio can be as high as 100:1 under low absorption, low scatter conditions with appropriate corrections for random coincidences and dead time. Thus, I-124 labeled antibodies or other agents can be imaged and quantified satisfactorily using PET. This may even be possible in the presence of larger therapeutic amounts of I-131.

The invention now being fully described, it will be apparent to one of ordinary skill in the art that many changes and modifications can be made thereto without departing from the spirit or scope of the invention as set forth herein.

We claim:

1. An in situ method of radiotherapy directed to a tumor associated antigenic site in a subject in need of such therapy, comprising detecting and localizing said tumor-associated antigenic site by an in vivo method for detecting and localizing a tumor-associated antigenic site in a subject in need of such detection, comprising administering to the subject an amount of an antigen-specific composition comprising a tumor-associated antigen-specific antibody or tumor-associated antigen-binding fragment thereof labeled with Iodine-124 at a site other than, and which does not significantly interfere with, the antibody-antigen binding site effective to localize the antigen antibody binding site;

scanning the subject body with an I-124 detector to attain the localization of the site; and thereafter in situ delivering a positron-emitting labeled antibody chelate to a subject, said chelate being capable of binding to either the I-124 tumor-associated antigen-binded labeled antibody or tumor-associated antigen-binding fragment thereof, or to the tumor associated antigen at an antigen site other than the antibody-antigen binding site.

2. The method of claim 1, wherein
    the composition is administered by injection.

3. The method of claim 2, wherein
    the composition is administered by intra-lymphatic injection.

4. The method of claim 1, wherein
    the antigen comprises a peritoneal tumor; and
    the composition is administered intraperitoneally.

5. A method according to claim 1, wherein said tumor-associated antigen-specific antibody or tumor-associated antigen-binding fragment comprises about 0.1 to 20 mCi of $I^{124}$ radiolabel/mg antibody or about 0.1 to 10 mCi of $I^{124}$ radiolabel/mg antigen-binding fragment.

6. The method of claim 1, wherein
    the composition is administered by injection; and
    the positron-emitting antibody chelate comprises about 0.1 to 20 mCi of radiolabel/mg antibody.

7. The method of claim 1, wherein
    the positron-emitting antibody chelate comprises an Iodine-124 labeled antibody chelate.

* * * * *